United States Patent [19]

Fumero et al.

[11] Patent Number: 5,044,901

[45] Date of Patent: Sep. 3, 1991

[54] PULSATILE PUMP FOR EXTRA-CORPOREAL CIRCULATION

[75] Inventors: Roberto Fumero, Basiglio; Lucio Perenzan, Bergamo, both of Italy

[73] Assignee: Bellco S.p.A., Modena, Italy

[21] Appl. No.: 573,272

[22] Filed: Aug. 27, 1990

Related U.S. Application Data

[63] Continuation of Ser. No. 462,292, Dec. 29, 1989, abandoned, which is a continuation of Ser. No. 228,671, Aug. 5, 1988, abandoned.

[30] Foreign Application Priority Data

Nov. 13, 1987 [IT] Italy ............... 22629 A/87

[51] Int. Cl.⁵ ............................................. F04B 43/12
[52] U.S. Cl. ................................. 417/474; 417/478; 417/479
[58] Field of Search .......... 417/478, 479, 510, 542, 417/474, 375; 251/9; 137/553, 554, 556

[56] References Cited

U.S. PATENT DOCUMENTS

| | | | |
|---|---|---|---|
| 1,922,196 | 8/1933 | Butler | 417/474 X |
| 1,988,624 | 1/1935 | Kipp | 417/478 |
| 2,412,397 | 12/1946 | Harper | 417/474 |
| 3,518,033 | 6/1970 | Anderson | 417/478 |
| 3,606,596 | 9/1971 | Edwards | 417/479 |
| 4,143,425 | 3/1979 | Runge | 417/412 |
| 4,156,437 | 5/1979 | Chivens et al. | 137/554 |
| 4,227,547 | 10/1980 | Cameron | 137/554 |
| 4,273,121 | 6/1981 | Jassawalla | 417/479 X |
| 4,293,961 | 10/1981 | Runge | 417/412 |
| 4,299,251 | 11/1981 | Dugas | 137/554 X |
| 4,303,376 | 12/1981 | Siekmann | 417/479 X |
| 4,364,716 | 12/1982 | Schjeldahl | 417/479 X |
| 4,382,753 | 5/1983 | Archibald | 417/479 |
| 4,479,760 | 10/1984 | Bilstad et al. | 417/479 X |
| 4,650,469 | 3/1987 | Berg et al. | 417/474 X |
| 4,657,490 | 4/1987 | Abbott | 417/479 X |
| 4,728,265 | 3/1988 | Cannon | 417/474 X |

FOREIGN PATENT DOCUMENTS 0941672 7/1982 U.S.S.R. ............... 417/474

Primary Examiner—Leonard E. Smith
Assistant Examiner—Eugene L. Szczecina
Attorney, Agent, or Firm—Oblon, Spivak, McClelland, Maier & Neustadt

[57] ABSTRACT

A pulsatile pump for extracorporeal circulation in cardiosurgery is disclosed, which is constituted by a housing chamber inside which a length of an elastic hose is inserted, which chamber is fitted with two squeeze valves, one of which is for suction (i.e. mitral valve) and the other of which is for delivery (i.e. aortic valve), and with an electropneumatically actuated plate which, in the systolic step partially compresses the hose by carrying out a rototranslational movement of the plate and, in the diastolic step moves away from the hose, with an analogous opposite movement of the plate, allowing the hose to relax. A microprocessor-control system makes it possible for the pump to operate, both in manual mode and in automatic mode, also in syntony with the patient's ECG.

8 Claims, 2 Drawing Sheets

PULSATILE PUMP FOR EXTRA-CORPOREAL CIRCULATION

This application is a continuation of application Ser. No. 07/462,292, filed on Dec. 29, 1989, now abandoned which is a continuation of application Ser. No. 228,671, filed on Aug. 5, 1988, now abandoned.

BACKGROUND OF THE INVENTION

1. Field of the Invention

The present invention relates to a pulsatile pump useable in cardiosurgery for extracorporeal circulation.

2. Discussion of the Background

More particularly, the object of the present invention is to provide a pulsatile pump essentially constituted by a housing chamber, inside which is inserted a length of an elastic hose, which chamber is fitted with two squeeze valves, i.e., a suction valve and a delivery valve, and with an electropneumatically-driven pusher body.

During the past ten years, the importance of inducing extracorporeal circulation which is as "physiologic" as possible was stressed by many studies. In particular, the choice of a pulsatile perfusion instead of a traditional, non-pulsatile perfusion, was regarded as superior as regards the reduction of the peripheral resistances (K. M. Taylor, J. Thorac. Cardiovas. Surg., 75, 569–83 (1978); J. Dunn, J. Thorac. Cardiovas. Surg., 68, 138–47 (1974); and H. Soroff, Arch. Surg., 98, 321–25 (1969)), the rapidity and uniformity of patient cooling and heating (G. D. Williams, J. Thorac. Cardiovas. Surg., 78, 667–77 (1979)), the reduction of the hormonal and metabolic disfunctions (W. F. Bremmer, J. Thorac. Cardiovas. Surg., 75, 392–99 (1978)), and the decrease of cerebral damage (K.M. Taylor, "Effects of pulsatile flow and arterial line filtration on cerebral cellular damage during open heart surgery", Open Heart Surgery, Springer Verlag, Berlino, 1982; and T. Matsumoto, Am. Surg., 1971, 61–64).

The need for realizing a pulsatile perfusion in order to obtain better operative and post-operative patient conditions, is particularly felt in infantile and pediatric cardio-surgery, owing to the greater criticity of the patient.

The use is known of pulsatile-flow pumps, which are obtained by means of suitable modifications supplied to the traditional peristaltic roller-pumps, or by coupling these latter in series to oscillating-flow pumps; such devices produce a so-to-speak "pulsed" flow, but are not in anyway capaole of realizing a truly pulsatile flow, i.e., such a flow as to ideally overlap to the physiologic flow, inasmuch as they do not realize a sufficiently short time rise time of the aortal pressure curve, and in the flow rate curve they show the typical ripples due to the separation of the rollers from the relevant seat. Furthermore, with such devices, the diastolic stroke of the pump necessarily coincides with the systolic stroke thereof, an adjustment of the flow curve during the suction stroke being hence impossible.

Furthermore, from U.S. Pat. No. 4,239,464 a pump is known, which is substantially different from the above discussed pumps, and realizes a truly pulsatile flow, by shifting the fluid column contained inside a length of flexible hose, by squeezing the latter by means of a plate. In order to prevent the reverse flow, at both hose ends two valves are provided, which consist of two plates which do rot squeeze the hose to a complete extent, but cause such a large pressure drop that the possibility of flowing back can be regarded as negligible. The movement of the squeezing plate, as well as the movement of the plates of the valves consists of a pure translation. Furthermore, as disclosed in said patent, it is driven by means of a cam system. By this type of pumps, the impulse frequence and the systolic discharge can be adjusted, and the synchronization with the patient's ECG can be established, whilst the ratio between the systole duration to the duration of the whole cycle, and the positioning of the systole inside said cycle cannot be changed, precisely owing to the system, by means of which the squeezing is accomplished (a system of volumetric type, with the movement drive being controlled by a cam outline).

SUMMARY OF THE INVENTION

The object of the present invention is to therefore provide a pump which generates a truly pulsatile flow, and which can be adjusted and controlled in such a way that the outline of the generated flow can ideally overlap to as large extent as possible to the physiologic flow.

The operating principle of the pump according to the present invention which fulfils such requisites, is based on the guided compression and relaxation of a length of elastic hose, housed inside a chamber fitted with squeeze valves. The pumping action is carried out by an electropneumatically-driven plate (or pusher), which realizes a rototranslational movement.

BRIEF DESCRIPTION OF THE DRAWING

A complete appreciation of the invention will be readily obtained when considered in connection with the accompanying drawings, wherein.

DESCRIPTION OF THE PREFERRED EMBODIMENTS

Figure 1A:
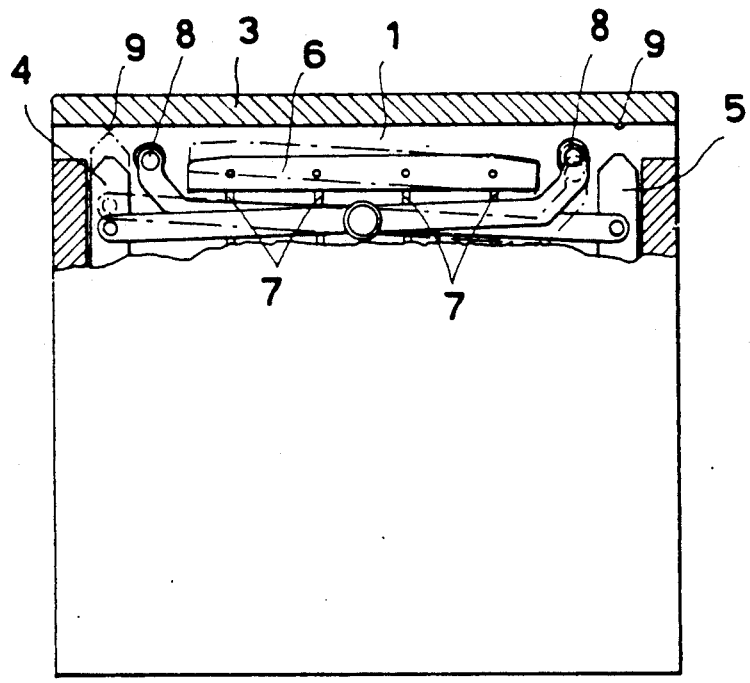
FIG. 1A is the pumping body.
Figure 1B:
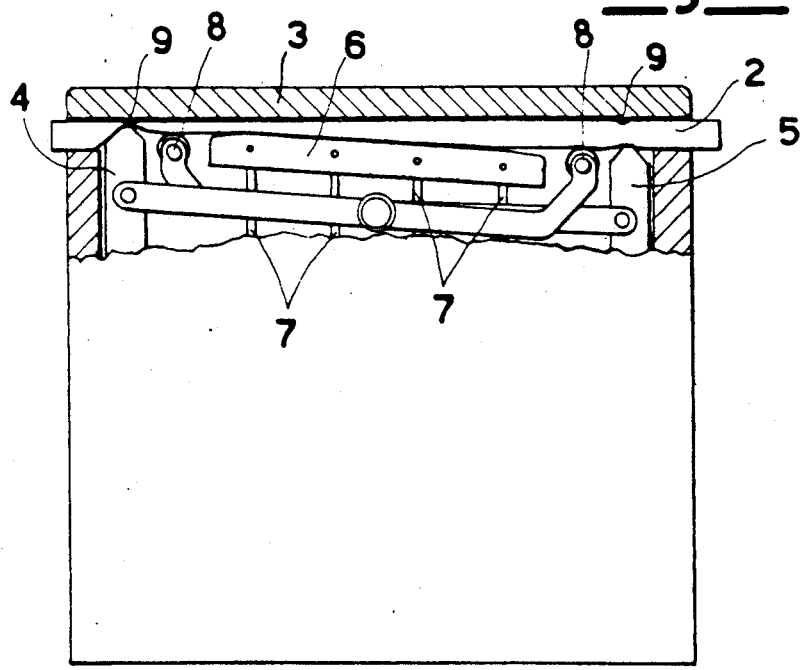
FIG. 1B is the pumping body in the systolic stroke.

More particularly, referring to FIGS. 1a) and 1b), which schematically show the pumping body and, in case of FIG. 1b), its operation in the systolic stroke, is constituted by a housing chamber (1) inside which a length of an elastic hose (2) is housed, which is in close contact with a support plate (3). This chamber is fitted with two squeeze valves, one of which is for suction (i.e. a mitral valve) (4) and the other of which is for delivery (i.e. an aortic valve) (5), and with a plate (or pusher) (6) which, in the systolic stroke (ejection) partially compresses the hose by performing a rototranslational movement controlled by the actuation, in a suitable succession, of four thrust stems (7).

The ejected volume is a function of the extent of hose squeezing, which is never total, and is controlled by the height reached by the pusher at systole end.

In the diastolic stroke (filling), the pusher moves downwards again, making it possible for the hose to elastically relax and therefore the fluid to be sucked from the intake end.

The valves and the pusher are actuated with compressed air by means of a hydraulic feed system, and the electrovalves are of on-off type.

More particularly, each one of both said valves is driven by a double-effect pneumatic cylinder. The cylinder is driven by two identical electrovalves, which must be excited in a complementary way.

Figure 2:
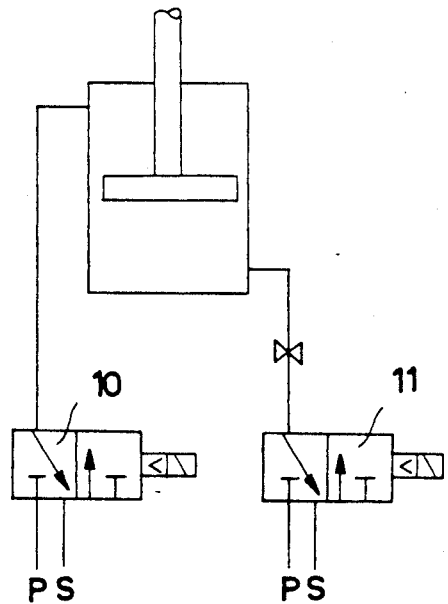
FIG. 2 is the schematic of the pneumatic circuit of the suction and delivery valves.

Referring to FIG. 2, which schematically shows the pneumatic circuit of a valve 4 or 5, in order that the valve may be closed, the electrovalve (11) must be energized and the electrovalve (10) must be de-energized; and vice-versa, if the valve has to be opened.

The advancement of the so-actuated valve closes the hose, by squeezing it against the support plate. Corresponding with each valve, the support plate is provided with a protrusion (9), so that the actual closure of the hose takes place owing to the compression between the same valve and the protrusion on the support plate.

According to a preferred form of practical embodiment, both the valve and the protrusion (9) are so shaped as to minimize the contact surface between the mutually opposite inner walls of the hose, thus reducing a possible cause of haemolysis.

According to a still more preferred form of practical embodiment, with each valve a volumetric compensator (8) is coupled, which is positioned on the opposite side relatively to the corresponding valve. This compensator has the purpose of inducing inside the hose (2) subject to the pumping action, a change in the inner volume equal to that induced by the movement of the valve, and of opposite sign. Such a volumetric compensator will be preferably constituted, as shown in FIGS. 1a) and 1b), by a cylinder freely revolutionary around its axis, fastened to an end of a rocker arm, at the other end of which the body of the squeeze valve is fastened. In such a way, when the valve is opened, at the opposite end a reduction will be caused in the volume of the hose, with a compensating effect, due to the pressure exerted by the cylinder on the hose, and, vice-versa, when the valve is closed, the moving away of the cylinder from the hose, with the consequent relaxation of the same hose, will produce a corresponding increase in the internal volume of the same hose, with an overall zero effect.

As an alternative, as the volumetric compensation means, an additional squeeze valve can be used, which is functionally connected with the main valve and moves in a contrary direction to the latter, which additional valve produces an opposite volume change in the length of hose in a far away position from the same valve.

The use of a volumetric compensator for each valve, serves to prevent the movements of closure and of opening of the valves which may cause movements of fluid towards the interior or towards the outside of the length of the elastic hose, movements which, among others, would cause very high speeds through very narrow areas, and hence high risk of haematic damages.

For example, the closure valve determines, at the closure time, a decrease in the available volume inside the inner portion of the hose. Such a decrease in volume, which, in the specific case, is slightly larger than 1 cc, would impose the ejection of such a volume from the interior of the hose through an orifice which is becoming smaller and smaller as the total closure of the valve is approached. Such a fact is detrimental from a fluid-dynamic and haemodynamic viewpoint, in that it involves high flowing speeds of the blood stream through the above-said orifice of progressively decreasing dimensions, speeds which tend to reach higher and higher values as the total closure of the valve is approaching. This drawback is extremely reduced, if not totally prevented, by the presence of the volumetric compensator (8), which, in case of valve closure, renders available, in a suitable position inside the hose, a volume equal to the volume which otherways would be expelled.

An identical and opposite action, obviously with identical advantageous fluid-dynamic and haemodynamic effects, is carried out by the compensator when the valve opens, by subtracting from the volume of the ventricular hose, a volume equal to the volume made available by the valve during the opening stroke.

The use of such valves equipped with volumetric compensators represents a further object of the present invention, independently from the particular type of pulsatile valve used.

These valves with compensators can in fact be adapted to other types of pumps too.

Figure 3:
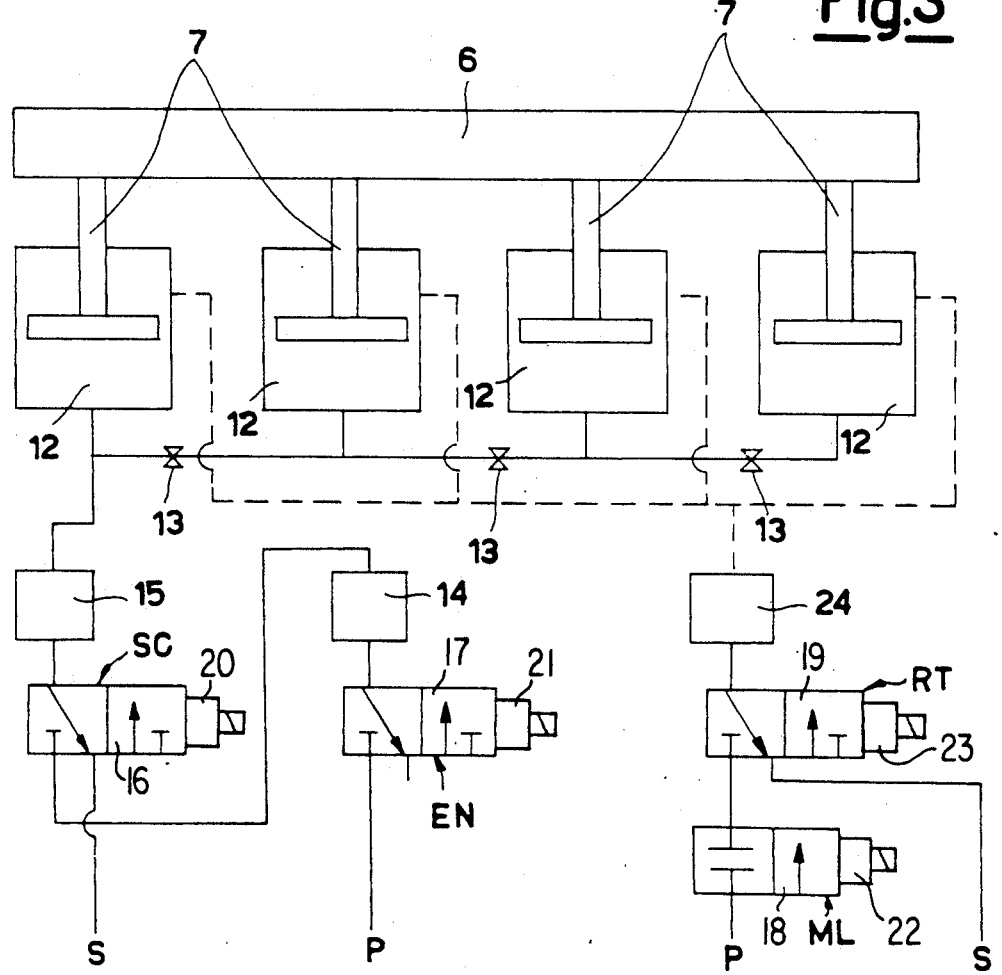
FIG. 3 is the schematic of the pneumatic circuit for the pusher.

Referring to FIG. 3, in the pump according to the present invention, the pusher (6) is driven by four double-effect pneumatic cylinders (7).

Its motion causes a variation in the internal volume of the hose (with a parabolic law, in first approximation, as a function of the advancement), and therefore a fluid suction, or a fluid ejection.

The large number of cylinders (which need not necessarily be four, as shown in FIG. 3 for exemplifying purposes, but can also be 2, or more than 4), and their distribution has the purpose of obtaining an oscillatory movement of the thrust plate: both ends (the end closer to the aortal valve, and the end closer to the mitralic valve) do not move together, but the end closer to the mitralic valve (the valve at the suction end) advances (and moves backwards) before the other. This particular movement presents much less risks, from a haemolytic point of view, than a simply translating plate, in that, with the flowrate being the same, larger surface areas are available for the fluid to flow with lower speeds.

The valves and the pusher are suitably energized with compressed air, by means of a hydraulic circuit and a system of control electrovalves.

In practice, compressed air available from a feed line is treated with a reducer filter with the automatic discharge of the condensate, so as to obtain dry air at the desired pressure, which is supplied to the control pneumatic system.

The oscillation of the pusher is obtained by installing throttling means (13) in the network feeding the cylinders (12), so that the farther cylinders are delayed relatively to the nearer cylinders, and the delay is adjusted by acting on the throttling means.

The compressed air necessary for actuating the cylinders which drive the pusher, will not be directly drawn from the feed line, but compressed air drawn from an energization tank (14) will be used. This energization tank, which substantially consists of a variable-volume chamber, is charged in its turn, more or less intensely according to needs, by drawing in a suitable and controlled way compressed air from the feed line. In fact, when compressed air from the line is used in order to actuate the cylinders, when the energization demand for the fluid to be pumped decreases, a time-controlled feed of compressed air to said cylinders has to be carried out. The smaller the energy demand will be, the shorter the time will be, during which compressed air is supplied to the cylinders. In such a way, the thrust action is concentrated during the first systolic stroke, during which all required ventricular ejection ends. From a physiologic viewpoint, on the contrary, it would be more suitable that such an ejection was determined by a less intense, longer-lasting energization. The use of the energization tank (14) makes it precisely possible for the cylinders and the thrust plate to be actuated with an adjustable feed pressure, adaptable to the various requirements.

Between the energization tank and the cylinders, two damping chambers (15) and (24) are inserted, which make it possible for a gradual and controlled increase of pressure inside the cylinders to take place. Such damping chambers generally consist of lengths of small-diameter hoses, wound to a spiral pattern, whose length and diameter depend on the desired damping. They are discharged at the end of each cycle, and they are empty at the onset of the following systole stroke, determining, owing to their integral pneumatic behaviour, a gradual and controlled increase in the pressure of the air fed to the cylinders.

In FIG. 3, the pusher-driving sub-unit is schematically shown. In this sub-unit, piloted pneumatic electrovalves ((16), (17), (18) and (19)) are used, and for each of them a pilot electrovalve ((20), (21), (22) and (23)) is used: the effect obtained is that it is necessary to control four electrovalves in order to obtain the reciprocating movement of the pusher; EN pressurizes the thrust chambers, SC discharges them; RT discharges the return chambers and ML pressurizes them. In order to obtain the advancement of the pusher with the compression of the hose (2), SC and EN must be energized (chambers under pressure) and RT must be de-energized (counter-chamber discharged), whilst, in order to obtain the return of the pusher, SC and EN must be de-energized (chambers discharged), and RT and ML must be energized (counter-chambers under pressure).

In particular, in FIG. 3:
SC = logic group of electrovalves 16, 20;
EN = logic group of electrovalves 17, 21;
ML = logic group of electrovalves 18, 22;
RT = logic group of electrovalves 19, 23.

The system indicated by the reference numeral (15) is the chamber damping the movement of advancement of the pusher, whilst, by the reference numeral (24), the chamber damping the return movement of the pusher is indicated.

Similar damping systems of viscous type were used for the suction and the delivery valves. This is used in order to prevent too fast a movement, harmful for blood, while simultaneously ensuring the complete closure of the valves without bleeding through them. In such a way, in fact, we succeeded in obtaining a gradual enough, but suitably fast, valve actuation, capable of securing a movement time of the order of 60/100 milliseconds, according to whether the valves are opened or closed.

According to a preferred form of practical embodiment, the pumping device is furthermore provided with photocells, which identify the exact point in time at which the valves begin to open or to close. The actuation of the valves is in fact characterized by a certain delay, substantially of a pneumatic type, derived from the need of introducing adequate amounts of pressurized fluid into the respective actuation pushers.

The photocells exactly identify the point in time at which the valves begin to open or to close, and this signal is sent to the control system, which compares it to the point in time at which the actuation was commanded, computes the delay of the one time point relatively to the other, and memorizes it; cycle after cycle, automatically, the actuation command will be anticipated by the so-computed time, so that the actual actuation of the valve takes place exactly at the desired time.

The pumping device is furthermore equipped with position sensors of the "Hall" type (in order to evaluate the position of the pusher) and with "switch" photocells, in order to evaluate the correct operation and the performances thereof, so as to have a feedback control action.

The optimum points in time of valve actuation depend in fact on several factors, some of which are bound to the need for reliable coverage of the strokes of closure of the same valves (a valve opens only after that the other valve is surely completely closed), other factors being bound to the movement of the thrust plate. As regards this latter aspect, it is important that the valve actuation means produce closures and openings in fluid-dynamically stationary positions of the thrust plate. The sensors a of "Hall" type make it possible the position of the thrust plate to be evaluated, and the time points of opening and of closure of the valves to be so positioned in time, so as to allow them to corresponding in an optimum way to the laws of movement of the thrust plate.

The control console, which consists of a set of devices for controlling and displaying the operating conditions of the pumping body, as well as possible external signals (ECG, arterial pressure), and of an electronic processor to which the above said information is continuously sent, constitutes the operating interface between the system and the operator, and manages the functions of the pumping body according to a suitable program.

The machine makes it possible for the pulsation frequency, the volume ejected at each beat and, consequently, the desired average flow, to be set. By entering some basic data relevant to the extra-corporeal loop (type and diameter of the cannula), and to the patient (weight and body surface area), such a machine is capable of supplying a correct perfusion, by selfcalibrating during the installation step, and of showing the actual flow rate values also in terms of cardiac indexes.

The length of hose used in the pump of the present invention may consist of any thermoplastic, biocompatible, material, endowed with such characteristics of elasticity and viscosity, as to enable it to be used in this particular field. A material, commonly used in the clinical field, which is well-suitable for the intended purpose, is Silastic ® (a silicone rubber marketed by Dow Corning). Other suitable materials are those disclosed, e.g., in U.S. Pat. No. 4,578,413.

When materials like these are used, which have such characteristics of elasticity and hardness as to allow the hose to spontaneously relax, at the end of the compression, so as to return back to its original shape and size, in a time compatible with the physiologic suction time, according to a preferred form of practical embodiment of the present invention, the hose is in no way constrained to the pusher.

Anyway, also other thermoplastic materials commonly used in the medical field can be used, which are endowed with characteristics of elasticity and hardness which are not sufficient to secure that the hose spontaneously relaxes in the required time; in such case, it will be necessary to constrain the hose to the pusher in such a way that both the compression and the subsequent relaxation take place in a guided way.

As regards the dimensions of the length of hose, these substantially depend on the dimensions of the patient.

The blood volume comprised between the two valves must in fact substantially correspond to the volume of blood ejected at each beat, i.e., to the systolic discharge. For use in infantile or pediatric cardiosurgery, therefore, hoses will be suitably used, the length of which is comprised within the range of from 20 to 45 cm, and whose diameter is comprised within the range of from ½ to ¾ inch. On the contrary, in case of an adult patient, instead of a length of hose having a circular cross-section and an even size, a length of hose will be better used which has an oval cross-section, or a kind of a bag/lung having an uniform cross-section.

It is understood that all these variations which can be supplied to the pump of the invention, as it is depicted in the hereto attached figures, in order to better fit it to the different situations, fall within the scope of the same invention.

We claim:

1. A pulsatile pump for extra-corporeal circulation in cardiosurgery, which comprises:
   a housing chamber in which a length of an elastic hose is inserted;
   two squeeze valves positioned in said chamber, one of which is for suction and the other of which is for delivery;
   an electro-pneumatically actuated plate which includes means in the systolic stroke for partially compressing the hose for carrying out rototranslational movement of said plate and, in the diastolic stroke for moving said plate away from the hose by an analogous opposite movement, so as to allow the hose to relax; and
   a set of pneumatic cylinders for controlling rototranslational movement of the plate.

2. A pump according to claim 1, wherein the set of cylinders which actuate the pusher comprise four cylinders.

3. A pulsatile pump for extra-corporeal circulation in cardiosurgery, which comprises:
   a housing chamber in which a length of an elastic hose is inserted;
   two squeeze valves positioned in said chamber, one of which is for suction and the other of which is for delivery;
   an electro-pneumatically actuated plate which includes means in the systolic stroke for partially compressing the hose for carrying out rototranslational movement of said plate and, in the diastolic stroke for moving said plate away from the hose by an analogous opposite movement, so as to allow the hose to relax; and,
   a volumetric compensator coupled with each of the valves wherein said compensator moves in an opposite direction to a direction of movement of the valve coupled thereto, so as to generate an equal and opposite volume change inside the length of hose in a remote position.

4. A pulsatile pump for extra-corporeal circulation in cardiosurgery, which comprises:
   a housing chamber in which a length of an elastic hose is inserted;
   two squeeze valves positioned in said chamber, one of which is for suction and the other of which is for delivery;
   an electro-pneumatically actuated plate which includes means, in the systolic stroke partially for compressing the hose for carrying out rototranslational movement of said plate and, in the diastolic stroke for moving said plate away from the hose by an analogous opposite movement, so as to allow the hose to relax; and
   compressed air generating means for pneumatically actuating the valves and the plate.

5. A pump according to claim 4, wherein the compressed air generating means comprises an air energizing tank for actuating the cylinders which is charged in turn with air drawn from a feed line.

6. A pump according to claim 5, which comprises damping chamber means located between the energization tank and the cylinders for actuating the plate and which includes means for supplying air pressure to the cylinders and increasing the supply of air in a gradual and controlled way.

7. A pulsatile pump for extra-corporeal circulation in cardiosurgery, which comprises:
   a housing chamber in which a length of an elastic hose is inserted;
   two squeeze valves positioned in said chamber, one of which is for suction and the other of which is for delivery;
   an electro-pneumatically actuated plate which includes means in the systolic stroke for partially compressing the hose for carrying out rototranslational movement of said plate and, in the diastolic stroke for moving said plate away from the hose by an analogous opposite movement, so as to allow the hose to relax; and
   at least one cylinder for controlling rototranslational movement of the plates wherein the means for actuating the valves comprise viscous damping chambers.

8. A pulsatile pump for extra-corporeal circulation in cardiosurgery, which comprises:
   a housing chamber in which a length of an elastic hose is inserted;
   two squeeze valves positioned in said chamber, one of which is for suction and the other of which is for delivery; and
   an electro-pneumatically actuated plate which includes means in the systolic stroke for partially compressing the hose for carrying out rototranslational movement of said plate and, in the diastolic stroke for moving said plate away from the hose by an analogous opposite movement, so as to allow the hose to relax; and
   at least one cylinder for controlling rototranslational movement of the plate wherein the length of hose is longer than the plate.

* * * * *